(12) United States Patent
Corzani et al.

(10) Patent No.: US 6,495,612 B1
(45) Date of Patent: *Dec. 17, 2002

(54) SHAPE-FORMED, THREE DIMENSIONAL, MOISTURE VAPOR PERMEABLE, LIQUID IMPERMEABLE ARTICLES

(75) Inventors: Italo Corzani, Chieti (IT); Gianfranco Palumbo, Bad Homburg (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/701,937

(22) PCT Filed: Jun. 9, 1999

(86) PCT No.: PCT/US99/13072

§ 371 (c)(1),
(2), (4) Date: Feb. 7, 2001

(87) PCT Pub. No.: WO99/64499

PCT Pub. Date: Nov. 16, 1999

(30) Foreign Application Priority Data

Jun. 9, 1998 (EP) .............................................. 98110596

(51) Int. Cl.$^7$ ................................................. C08L 5/22
(52) U.S. Cl. ...................................... 523/105; 523/111
(58) Field of Search ................................ 524/312, 315, 524/385, 386, 387, 389; 523/105, 111

(56) References Cited

U.S. PATENT DOCUMENTS

| | | | | |
|---|---|---|---|---|
| 4,854,995 A | * | 8/1989 | Kasper et al. | 156/243 |
| 5,753,782 A | * | 5/1998 | Hammond et al. | 525/450 |
| 5,948,707 A | * | 9/1999 | Crawley et al. | 442/101 |
| 6,107,537 A | * | 8/2000 | Elder et al. | 604/364 |
| 6,133,400 A | * | 10/2000 | Helmke | 528/83 |

FOREIGN PATENT DOCUMENTS

| | | |
|---|---|---|
| EP | 0 805 182 A1 | 4/1997 |
| EP | 0 806 283 A2 | 12/1997 |
| WO | WO 96/25902 | 8/1996 |

* cited by examiner

*Primary Examiner*—Edward J. Cain
*Assistant Examiner*—Katarzyna Lee
(74) *Attorney, Agent, or Firm*—Bart S. Hersko

(57) ABSTRACT

The present invention relates to shape-formed three dimensional articles which are moisture vapour permeable and liquid impermeable and comprise liquid impermeable formed structures having an enhanced moisture vapour permeability and comprising thermoplastic compositions having a higher processability. The shape-formed three dimensional articles of the present invention can find a variety of applications wherein moisture vapour permeability combined with liquid imperviousness are desirable.

10 Claims, No Drawings

SHAPE-FORMED, THREE DIMENSIONAL, MOISTURE VAPOR PERMEABLE, LIQUID IMPERMEABLE ARTICLES

FIELD OF THE INVENTION

The present invention relates to shape-formed three dimensional articles which are moisture vapour permeable and liquid impermeable and comprise liquid impermeable formed structures having an enhanced moisture vapour permeability and comprising thermoplastic compositions having a higher processability. The shape-formed three dimensional articles of the present invention can find a variety of applications wherein moisture vapour permeability combined with liquid imperviousness are desirable.

BACKGROUND OF THE INVENTION

Articles comprising structures which provide a liquid barrier in addition to providing moisture vapour permeability are known in the art. Particularly preferred for this type of moisture vapour permeable, liquid impermeable articles are hydrophilic thermoplastic compositions forming a continuous structure, e.g. a continuous film that does not allow the flow of moisture vapour through open pores or apertures in the material, but does transfer substantial amounts of moisture vapour through the film by absorbing water on one side of the film where the moisture vapour concentration is higher, and desorbing or evaporating it on the opposite side of the film where the moisture vapour concentration is lower.

For example WO 95/16746 discloses films prepared from mixtures of a) block copolyether ester, block copolyether amides (e.g. Pebax™) and or polyurethane and b) thermoplastic polymer which is incompatible with (a), and c) a compatibiliser. The films are liquid impermeable and have moisture vapour permeability of about 700 g/m$^2$·day. Also, U.S. Pat. No. 5,447,783 discloses a vapour permeable water resistant multi component film structure having at least three layers. The outer layers are hydrophobic copolyetherester elastomers having a thickness of 1.3–7.6 micrometers and a WVTR of 400–2500 g/m$^2$·24 h and the inner layer is a hydrophilic copolyetherester elastomer having a thickness of 7.6–152 micrometers and a WVTR of at least 3500 g/m$^2$·24h.

U.S. Pat. No. 5,445,875 discloses a waterproof, bloodproof and virusproof breathable laminate. The laminate comprises a woven/nonwoven fabric and an extruded film such as Hytrel™ having a thickness of about 1 mil (25.4 micrometers).

Other composite laminates are described for example in U.S. Pat. No. 5,599,610 which discloses tri-laminated fabric for surgical gowns comprising outer layers of woven fabric and an inner layer of a microporous polyurethane membrane. The microporous film has a thickness of 12–55 micrometers and a MVTR of 1100 g/m$^2$·24 h upright and 5500 g/m$^2$·24 h inverted (ASTM E96-B). Polyetherpolyurethane adhesive is used to join the layers.

Similarly, U.S. Pat. No. 5,532,053 discloses a high moisture transmission medical film which can be laminated onto a nonwoven material. The laminate film comprises a first layer of polyetherester copolymer and second and third layers selected from a specified group of polymers. The film has a MVTR of greater than 750 g/m$^2$·24 h (ASTM F1249) and a thickness of less than 1 mil (25.4 micrometer) preferably 0.6 mil to 0.75 mil (15–19 micrometers).

U.S. Pat. No. 4,938,752 discloses absorbent articles comprising films of copolyether esters which have reduced water permeability, a water vapour permeability of 500 g/m$^2$·24 h (as measured in a specified described test) and a thickness of 5–35 micrometers. There is no disclosure of a supportive substrate.

U.S. Pat. No. 4,493,870 discloses a flexible layered waterproof product comprising a textile material covered with a film of a copolyetherester having an MVTR of at least 1000 g/m$^2$·24 h (ASTM E96-66) having a thickness of 5 to 35 micrometers.

GB 2024100 discloses a flexible layered water resistant article comprising a microporous hydrophobic outer layer which is moisture vapour permeable but resist liquids and a hydrophilic inner layer of polyetherpolyurethane having a MVTR of above 1000 g/m$^2$·24 h.

In our patent application entitled "Shape-formed, three dimensional, moisture vapour permeable, liquid impermeable articles comprising moisture vapour permeable, liquid impermeable structures comprising low viscosity thermoplastic compositions" filed on the same day as the present application (P&G case CM2131F), shape-formed three dimensional articles are disclosed comprising thermoplastic compositions for making hydrophilic continuous moisture vapour permeable, liquid impermeable structures, e.g. layers, comprised in said articles, having preferred characteristics of moisture vapour permeability and liquid imperviousness. The thermoplastic compositions comprise preferred thermoplastic polymers such as polyurethanes, polyether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof. The disclosed preferred thermoplastic compositions are also readily processable so as to provide a moisture vapour permeable liquid impermeable structure, to be comprised in the shape-formed article, by means of known methods, e.g. by coating a suitable layer having the desired thickness onto a substrate, so facilitating the processing of said thermoplastic composition in the manufacture of said articles, for example avoiding the need of complex processing equipment such as extrusion apparatuses. This is achieved by modifying the viscosity of the thermoplastic polymers by means of the inclusion in the composition of a suitable plasticiser that lowers such viscosity. This allows to utilise with these preferred thermoplastic compositions process conditions for the selected forming method which are less demanding in terms of temperature and pressure, e.g. those known in the art for the direct coating of low viscosities hot melts onto a substrate in order to form a moisture vapour permeable, liquid impervious structure in form of film or layer.

It has surprisingly been discovered that by suitably selecting the plasticiser or blend of plasticisers in the thermoplastic composition a shape-formed three dimensional moisture vapour permeable liquid impervious article can be obtained comprising a moisture vapour permeable, liquid impermeable structure, e.g. a film or layer, which comprises said thermoplastic composition and has an enhanced moisture vapour permeability if compared to a corresponding structure comprising a thermoplastic composition not comprising the plasticiser or blend of plasticisers. Of course the preferred plasticiser or blend of plasticisers can also adjust the viscosity of the thermoplastic composition to allow the formation of said structure, e.g. in form of a film or a layer, from the thermoplastic composition by means of a simplified process.

SUMMARY OF THE INVENTION

The present invention relates to a shape-formed, three dimensional, moisture vapour permeable, liquid impermeable article comprising a moisture vapour permeable, liquid impermeable structure comprising a thermoplastic composition. The thermoplastic composition comprises: a thermoplastic polymer or mixture of polymers selected from the group consisting of polyurethanes, poly-ether-amides block copolymers, polyethyleneacrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, or mixtures thereof, a suitable compatible hydrophilic plasticiser or blend of hydrophilic plasticisers,
wherein the thermoplastic composition has a viscosity of from 50 poise to 4000 poise at a frequency of 1 rad/s at a temperature of 210° C. or less and a viscosity of less than 2000 poise at a frequency of 1000 rad/s at a temperature of 210° C. or less,
wherein the hydrophilic plasticisers are selected from the group consisting of acids, esters, amides, alcohols, polyalcohols, or mixtures thereof.

DETAILED DESCRIPTION OF THE INVENTION

According to the present invention, shape-formed, three dimensional moisture vapour permeable liquid impermeable articles are provided which comprise moisture vapour permeable, liquid impermeable structures comprising highly processable thermoplastic compositions, and also having an enhanced moisture vapour permeability.

The highly processable thermoplastic compositions can comprise the majority or sole material of the shape-formed three dimensional article of the present invention. In the latter case, the structure is entirely made of the thermoplastic composition, and in turn the article is entirely constituted by the structure. Alternatively, the thermoplastic compositions can be utilised in combination with one or more other materials to create a composite structure comprised in the article, or also the thermoplastic composition can constitute entirely a structure, which is then combined with other elements in the article of the present invention. In many cases, it may be preferred that the shape-formed article be comprised substantially or wholly by the thermoplastic composition, which can provide structure without use of additional materials.

Said thermoplastic compositions are useful in the incorporation into the articles of the present invention which are shape-formed, three dimensional as delivered to the consumer. Said articles therefore possess at least one region that displays some three dimensional form or shape in contrast to a two dimensional or planar form. Such three dimensional form or shape may involve simple or complex surface geometries. Examples to illustrate the range include simpler constructions such as two planes joined at a line defining a right (90 degree) angle or a simple sphere to more complex constructions such as two wave form surfaces intersecting in a non-linear fashion.

Said shape formed articles may be shaped in a closed form, such as a spherical ball or a cube, or shaped with one or more openings, such as a hand covering or glove.

In response to an introduced force or pressure, the article may display deformation, that is change or alter its shape. Though not limited to the following definitions, such deformation can be thought of as a general expansion or contraction of the overall article, in one way measured by a change in enclosed volume within the general boundaries of the surfaces of the article or alternatively measured by a change in the volume of the circumscribed space as defined by the outermost surfaces of the article.

Such introduced forces or pressures include, but are not restricted to, externally or internally applied pressure increases or decreases (vacuum); mechanical compression forces; and, tensile forces being applied within the articles walls themselves (i.e. stretching a portion of the article wall).

Once the applied force or pressure is removed, the post-deformation response of the article can range from full shape recovery to an irreversible shape change.

Such articles can be re-used many times or be so constructed that the intended article life is but one use before disposal or refurbishment.

The shape-formed, three dimensional articles of the present invention can be employed in a variety of usage areas particularly when water vapour permeation is needed but liquid barrier protection is still desired. There are other usage situations where the articles of the present invention employing the thermoplastic composition can provide other barrier functions such as pathogen barrier, barrier to undesirable or hazardous chemicals such as those causing a deleterious effect on human skin, or provide selective barrier for other specific elements to be blocked such as specific chemicals, gasses or biological entities.

The following paragraphs provide example categories of use where the articles of this invention can provide useful advantage. The listing of categories is intended for illustration purposes and is not all-inclusive and therefore is not limiting.

As an illustrative example, one category of shape-formed, three dimensional articles beneficial to humans and other living creatures are bodily protective, hygienic or comfort articles such as, but not limited to: hand coverings such as gloves, finger cots, mitts, mittens; foot or leg coverings such as socks, hose, pantyhose, shoes, slippers; head coverings such as hats, caps; prophylactic articles such as condoms, semen shields internally placed inside the vaginal cavity; face coverings such as face masks, nose covers, ear covers or mitts; body support items such as male organ "athletic" supporters, brassieres; formed clothing for use as underwear, protective sleeves, or as a part of or wholly incorporated into protective pads. Other example articles and applications include but are not limited to: flexible or drapable clothing articles for humans or other living creatures such as the non-limiting examples of shirts, pants, undergarments, bibs, smocks, coats, scarves, body wraps, stockings, leggings, skirts, dresses, etc.; other flexible or drapable clothing for various tasks and occupations including medical professions, agricultural jobs, mechanical assembly and repair, emergency public services, the military, athletic endeavours, cleaning positions, etc.

A preferred category of shape-formed, three dimensional articles according to the present invention comprises said hand covering articles, and more specifically gloves, also including gloves made of two flat material portions, at least one material portion comprising the structure of this invention, which are joined around a common perimeter typically defining the shape of a hand, and which later take a fuller, higher volume three dimensional shape when a hand is inserted during later use through an opening comprised in said perimeter.

Another example category of use involves packaging such as with food products such as fresh produce and baked goods (bread, rolls, cakes) as non-limiting examples.

A further example category of use involves agriculture and horticulture such as, as non-limiting examples, an individual article (container, three dimensional "bag") which is placed to partially or totally enclose an individual or specific group of plants.

An even further example category of use involves protective furniture coverings such as protective covers for upholstered chairs and sofas, etc.

Said shape-formed, three dimensional articles of the present invention can be formed or shaped by a variety of known thermoplastic forming methods. A class of such methods is generally described as "moulding" where the material is often shaped via use of male or female moulds or combinations of moulds. Depending on the technique, certain processing temperature and pressure (or vacuum) conditions may be preferred for production of a given article. Such known moulding methods include, but are not limited to: dip moulding, blow moulding, injection moulding, compression moulding, thermoforming, vacuum thermoforming, extrusion moulding, rotational moulding, slush moulding, etc.

Afterward, the article and mould(s) are separated. Often there may be an intervening process step between contact of the thermoplastic composition and separation of the shape formed article and mould. The nature of the intervening step or steps will vary depending on moulding technique, environmental condition, material format, etc. For example, a dip moulded article may need to be processed to remove: (i) solvent from the article if a solvent-based format of the raw material form of the thermoplastic composition is chosen; (ii) water from the article if a emulsion-based format of the raw material form of the thermoplastic composition is chosen; or, (iii) heat if a hot melt format of the raw material form of the thermoplastic composition is chosen. Of course this further removing process step can be applied to any of the known forming methods described herein with reference to the thermoplastic compositions of this invention (e.g. moulding, or casting, or coating).

Other known methods for producing the shape-formed, three dimensional articles of the present invention, namely for processing the thermoplastic compositions comprised herein, also include: film and sheet casting; blown film techniques; an additional tentering process step; an additional calendering step; an additional quenching step; an additional heat treatment step; etc. The nature of the specific production conditions or type or order of process steps will vary depending on the chosen making technique, environmental condition, material format, etc. For example, a process step may need to be included to remove: (i) solvent; (ii) water; or, (iii) heat as explained above with reference to the dip moulding process.

Regarding casting, the thermoplastic composition may be cast onto a moving cylinder, belt, web, release substrate (including release papers and films), etc. into e.g. a film or sheet. The film or sheet can be later separated from the casting surface.

A film or sheet can be produced with two or more layers where at least one of the layers comprises the thermoplastic composition of this invention. This can be accomplished by a variety of known means, including but limited to: co-extrusion, extrusion coating, etc.

The resulting materials can are then typically post formed into a shaped form such as by thermoforming, vacuum thermoforming, and other known processing methods for shaping or forming thermoplastic films and sheets.

While it may be at times preferable that the entire shape-formed portion of the three dimensional article of the present invention be comprised solely of the thermoplastic composition, the article can be a composite with one or more other materials. The composite, for example, can involve two or more components of the specific thermoplastic composition within the present invention or different specific thermoplastic compositions of the present invention.

Alternatively, the composite can involve at least one component of the thermoplastic composition in combination with one or more other materials. Such materials include, but are not limited to: fibres, fibrous batts, non-wovens, wovens, papers, metal foils, micro-porous or porous membranes, films such as polymeric films, inorganic structures such as compressed gypsum sheets, perforated or apertured films and papers, macroscopically expanded films, cloth, substantially rigid fibre-based materials such as lumber, etc.

Said other components may be non-absorbent, absorbent, liquid-containing, etc.

Preferably the composite structures described above have a moisture vapour transfer rate of at least 100 g/m$^2$·24 h, more preferably at least 300 g/m$^2$·24 h, and most preferably at least 500 g/m$^2$·24 h.

Said composite can be assembled later after at least two separate components of the shape-formed, three dimensional article of the present invention have been partially or wholly processed, with at least one of said components being of the thermoplastic composition. Such components can be brought together in a variety of known approaches including but not limited to: sealing such as heat sealing, ultrasonic or pressure bonding or welding, RF sealing, laser sealing, etc.; crimping; adhering via use of adhesives, glues, reactive bonding materials, wetting with water or other liquids, etc.; mechanical fastening or connection via hook and loop systems, nails, staples, hardware fasteners such as hook & grommet or bolt and nut; etc.; use of attractive forces including electromagnetic forces (e.g. magnetism) and electrical charge (e.g. static electricity).

Alternatively or in addition, other material(s) can be introduced during the thermoplastic composition forming process, e.g. moulding, to allow concurrent mating with the other material(s) into a composite article during the shape forming step. A second material could be e.g. introduced which comprises numerous separate individual pieces, for example fibres. As a non-limiting example, a portion of the surface of the article can be contacted during the moulding process with a fibrous material to create a flocked surface without need for conventional adhesives normally used for flocking. An example product would be a glove.

Another useful technique is the process of spray coating. The thermoplastic composition of this invention lends itself to a heated spraying technique whereas upon heating the viscosity is sufficiently lowered to allow spray coating or sputtering. Such thermoplastic composition spray coating can occur with the aid of a mould, either male or female, to build surfaces or walls of the article. Afterward, the article and mould (or mould parts) are separated from each other. Alternately, the spray coating method can employ different starting raw material formats of the polymer composition such as a solvent -based approach or an emulsion.

For a composite article employing the spray coating approach, the other material may provide sufficient three dimensional structure by itself such that the other material acts as the mould, after which it is sufficiently coated the composite article is complete, avoiding the beforementioned separation of article from mould. Said combined article component and mould can also comprise a flattened glove liner that may lie somewhat flat during polymer introduction, for example via spray coating, and then later takes a fuller, higher-volume shape when a hand is inserted during later use.

The thickness of the shape-formed article of this present invention can be constant or vary within the structure . Though not limited to any specific thickness range, depending upon application there may be preferred ranges. For example, the preferred range for a worn personal hygiene article may desirously range from as thick as 400 microns down to less than 0.5 microns and more preferably, in certain cases, substantially less than 0.5 microns. In contrast, a construction or even packaging application may, for certain reasons, dictate a preferred range from 200 to 2000 microns or even thicker.

Said article can possess areas where no polymer is present ranging from voids so small to be considered micro-porous to larger scale, macroscopic-sized voids. A portion or all of the article's surface can be apertured whereas the apertures can be a rather simple geometry like a hole or slit; or, the discrete apertures can extend beyond the horizontal plane of the surface. As an example, the protuberances can have an orifice located at its terminating end. As further example, said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured performed films are uni directional such that they have at least substantially, if not complete one directional fluid transport.

Suitable thermoplastic polymers comprised in the thermoplastic composition of this invention include polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids and derivatives, ionomers, polyethylene-vinyl acetate with a vinyl acetate content of more than 28 weight %, polyvinyl alcohol and its copolymers, polyvinyl ethers and their copolymers, poly-2-ethyl-oxazoline and derivatives, polyvinyl pyrrolidone and its copolymers, thermoplastic cellulose derivatives, and mixtures thereof.

Particularly preferred thermoplastic polymers are thermoplastic poly-ether-amide block copolymers (e.g. Pebax™), thermoplastic poly-ether-ester-amide block copolymers, thermoplastic polyester block copolymers (e.g. Hytrel™), thermoplastic polyurethanes (e.g. Estane™), or mixtures thereof.

Such thermoplastic polymers or mixture of polymers can be typically highly viscous in the melted state at the process conditions that are typical of the known processes of film or layer formation, e.g. an extrusion process involving a high power screw extruder. For example they may have a viscosity higher than 5000 poise at a temperature of 20° C. above the DSC (Differential Scanning Calorimetry) melting point, which is the temperature identified as that corresponding to the DSC peak, or corresponding to the highest DSC peak in case of a mixture of polymers showing more than one peak, and at a frequency of 1 rad/sec.

The viscosity of the thermoplastic compositions comprised in the shape-formed, three dimensional articles of the present invention and comprising the preferred thermoplastic polymers or mixture of polymers can be preferably adjusted by including in the thermoplastic composition a suitable plasticiser, or blend of plasticisers, that is compatible with the thermoplastic polymers and that lowers the viscosity of the thermoplastic polymer or mixture of polymers in the melted state.

The thermoplastic compositions of this invention comprising the preferred hydrophilic plasticiser or blend of hydrophilic plasticisers have the following complex viscosities ($\eta^*$):

50 poise $<\eta^*<$4000 poise, preferably 100 poise $<\eta^*<$2000 poise, more preferably 100 poise $<\eta^*<$1000 poise, at a frequency of 1 rad/s at a temperature of 210° C. or less and $\eta^*<$2000 pose, preferably $\eta^*<$1000 poise, more preferably $\eta^*<$500 poise, at a frequency of 1000 rad/s at a process temperature (T) of 210° C. or less, wherein $\eta^*$ represents the complex viscosity of the thermoplastic polymeric composition. Preferably the temperature T is 200° C. or less and more preferably 180° C. or less and most preferably from 200° C. to 50° C.

The thermoplastic compositions having the complex viscosity described are more easily processable in order to provide the moisture vapour permeable, liquid impermeable structures comprised in the articles of the present invention. For example, said thermoplastic compositions allow for a film or layer to be e.g. coated onto a substrate using typical coating conditions and apparatuses known in the art for the coating of low viscosity hot melt compositions in a layer having a required thickness onto a substrate, while also keeping the advantageous characteristics of the preferred thermoplastic polymers in providing hydrophilic continuous moisture vapour permeable, liquid impermeable layers or films. Other known methods for making three dimensional articles such as moulding, casting, and others as described above, also take advantage from the lower viscosity of the thermoplastic compositions comprised herein.

Thermoplastic compositions having such viscosities can also provide very thin films or layers.

It has been surprisingly found that by selecting the hydrophilic plasticiser or blend of hydrophilic plasticisers to be comprised in the thermoplastic composition from the group consisting of acids, esters, amides, alcohols, polyalcohols, or mixtures thereof, the advantage of an enhanced moisture vapour permeability of the resulting structure, e.g. a layer or a film, formed from the thermoplastic composition is achieved, when compared to a corresponding structure formed from a thermoplastic composition comprising the same thermoplastic polymer, but without the plasticiser.

The preferred hydrophilic plasticiser or blend of hydrophilic plasticisers can also adjust the viscosity of the thermoplastic composition to the preferred values in order to facilitate the processing of the thermoplastic composition by means of one of the above described methods, for example making it processable by coating said thermoplastic composition onto a substrate in a layer or film having a desired thickness, in order to form the moisture vapour permeable liquid impermeable structure comprised in the shape-formed three dimensional moisture vapour permeable liquid impermeable article of the present invention.

Preferred hydrophilic plasticisers according to the present invention are esters of citric acid, tartaric acid, maleic acid, sorbic acid, fumaric acid, lactic acid, glyceric acid, malic acid; glycerol and its esters; sorbitol; glycolates; and mixtures thereof.

Preferably the thermoplastic composition comprised in the shape-formed three dimensional moisture vapour permeable liquid impermeable articles of the present invention comprises from 10% to 80%, more preferably from 25% to 70% by weight of the thermoplastic composition, of the thermoplastic polymer or mixture of polymers, and from 20% to 90%, preferably from 30% to 75% by weight of the thermoplastic composition, of the suitable hydrophilic plasticiser or blend of hydrophilic plasticisers.

The thermoplastic compositions comprised in the shape-formed three dimensional moisture vapour permeable liquid impermeable articles of the present invention may in addition comprise additional optional components to further improve the processability of the compositions and also the mechanical characteristics as well as other characteristics as tackiness, resistance to ageing by light and oxygen, visual appearance etc., of the structures, e.g. films or layers, formed from such thermoplastic compositions.

Such optional components include tackifying resins or blends of tackifying resins having a softening point of 125° C. or less. Preferred resins, which may be present by up to 50% by weight of the thermoplastic composition, may be selected from rosins and rosin esters, hydrocarbon resins, aliphatic resins, terpene and terpene-phenolic resins, aromatic resins, synthetic $C_5$ resins, mixtures of synthetic $C_5$–$C_9$ resins, and mixtures thereof. Other optional components of said thermoplastic compositions include anti-oxidants, anti-ultraviolets, pigments and mixtures thereof, which may be present within the composition at a level of up to 10% by weight of the composition.

A thermoplastic composition comprised in the moisture vapour permeable liquid impermeable structures, in turn comprised in the shape-formed three dimensional moisture vapour permeable liquid impermeable articles according to the present invention can be manufactured with a process that will typically comprise the steps of providing the thermoplastic polymer or mixture of polymers and the suitable plasticiser or blend of plasticisers, heating the components and compounding them, e.g. with a known suitable mixer to form the thermoplastic composition in the molten state having the desired complex viscosity $\eta^*$.

According to the present invention a moisture vapour permeable, liquid impervious structure, e.g. in the form of a layer, can be formed from the thermoplastic composition described above for example by coating said thermoplastic composition onto a substrate.

The moisture vapour permeable liquid impermeable structures, e.g. in form of films or layers, comprising said thermoplastic compositions preferably have a moisture vapour transport rate of at least 100 g/m²·24 h, preferably at least 300 g/m²·24 h, most preferably at least 500 g/m²·24 h.

A process for making a moisture vapour permeable liquid impermeable structure, e.g. in form of a layer or film, from a thermoplastic composition which is intended to be comprised in a shape-formed three dimensional moisture vapour permeable liquid impermeable article according to the present invention can for example comprise the steps of providing said composition, heating it to make it flowable, and coating said composition in the molten state onto a substrate in a layer having the desired thickness. The structure can be included or formed into a shape-formed three dimensional moisture vapour permeable liquid impermeable article according to the present invention, e.g. hand covering articles such as finger cots, mitts, mittens, gloves, or other articles as described above, by means of one of the method known in the art. While said substrate can be simply a formation substrate, onto which the thermoplastic composition is coated in order to form a film or layer of the desired thickness which is subsequently separated from said substrate and used as such, in an embodiment of the present invention a moisture vapour permeable, water impervious composite structure can also be formed which comprises the thermoplastic composition and a substrate onto which said thermoplastic composition is coated, wherein the substrate is also preferably moisture vapour permeable.

Such embodiment of the present invention provides a moisture vapour permeable, liquid impervious composite structure, comprised in a shape-formed three dimensional moisture vapour permeable liquid impermeable article, wherein the contribution of the layer formed from the thermoplastic composition of the present invention to the performance of the composite material resides only in the provision of a liquid barrier and hence could be advantageously provided as thinly as possible. The remaining performance physical criterion being preferably provided by the provided substrate, that therefore preferably acts also as a support layer.

The substrate, or support layer may be any useful layer which is preferably also moisture vapour permeable, preferably having a moisture vapour permeability of at least 100 g/m²·24 h, more preferably at least 300 g/m²·24 h, and most preferably at least 500 g/m²·24 h.

Suitable substrates for use herein as support layers include two dimensional, planar micro and macro-porous films; macroscopically expanded films; formed apertured films; nonwoven and woven layers. According to the present invention the apertures in said layer may be of any configuration, but are preferably spherical or oblong and may also be of varying dimensions. The apertures preferably are evenly distributed across the entire surface of the layer, however layers having only certain regions of the surface having apertures are also envisioned.

Suitable two dimensional porous planar layers of the backsheet may be made of any material known in the art, but are preferably manufactured from commonly available polymeric materials. Suitable materials are for example Gore-teX™ or Sympatex™ type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term two dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in the already mentioned U.S. Pat. No. 3,929,135.

Suitable macroscopically expanded films for use herein include films as described in for example in U.S. Pat. No. 4,637,819 and U.S. Pat. No. 4,591,523.

Preferred support layers for use herein include woven and nonwoven layers, most preferably hydrophobic fibrous layers such as hydrophobic nonwoven.

The composite moisture vapour permeable structures of this embodiment of the present invention are particularly advantageous as they allow the possibility of providing a composite wherein the thermoplastic composition may be coated onto the support substrate as a layer with the desired thickness. Typical coating conditions and apparatuses known in the art for the direct coating of low viscosities hot melts can be readily utilised in order to provide the thermoplastic composition at the desired thickness.

A possible method for forming a composite laminate by coating the thermoplastic composition onto a substrate acting as a support layer is described in PCT application WO 96/25902.

At least at the coating temperature, the thermoplastic composition in form of a layer preferably exhibits adhesive properties on the supportive substrate in order to form the moisture vapour permeable composite structure such that no additional adhesive is required to achieve a permanent attachment between the thermoplastic composition and the substrate. In some applications it may be also desirable that the thermoplastic composition remains tacky at any temperature i.e. it is formulated so to have the typical characteristics of a pressure sensitive adhesive.

The shape-formed three dimensional moisture vapour permeable liquid impermeable articles of the present invention comprising the moisture vapour permeable liquid impermeable structures in turn comprising the low viscosity thermoplastic compositions described above find utility in a number of applications wherein liquid imperviousness and moisture vapour permeability are desirable. In particular the present invention can be effectively utilised within shape-formed three dimensional moisture vapour permeable liquid impermeable articles such as e.g. hand covering articles comprising finger cots, mitts, mittens and preferably gloves, and also other articles as described above. Preferably the moisture vapour permeable, liquid impervious structures, e.g. layers or composites, formed from the thermoplastic compositions described so far and comprised in the shape-formed three dimensional moisture vapour permeable liquid impermeable articles of the present invention have a moisture vapour transfer rate of at least 100 g/m$^2$·24 h, more preferably at least 300 g/m$^2$·24 h, and most preferably at least 500 g/m$^2$·24 h.

The preferred hydrophilic plasticisers of this invention can also be added to thermoplastic polymers which are not intrinsically moisture vapour permeable, such as polyolefins, e.g. polyethylene or polypropylene, or styrenic block copolymers, which are all substantially both moisture vapour and liquid impervious, in order to provide the final thermoplastic composition with moisture vapour permeability.

According to the present invention the complex viscosity $\eta^*$ is measured using a Rheometer RDA-II available from Rheometrics Co. Moisture vapour permeability is measured as Water Vapour Transmission Rate (WVTR) at 23° C. according to the ASTM E-96 "Upright Cup" method.

What is claimed is:

1. A shape-formed, three dimensional, moisture vapour permeable, liquid impermeable article comprising a moisture vapour permeable, liquid impermeable structure, wherein said structure is in the form of a continuous thin film, said structure comprising a thermoplastic composition, said composition comprising:

a thermoplastic polymer or mixture of polymers selected from the group consisting of polyurethanes, poly-ether-amides block copolymers, polyethylene-acrylic acid copolymers, polyethylene oxide and its copolymers, poly lactide and copolymers, polyamides, polyester block copolymers, sulfonated polyesters, poly-ether-ester block copolymers, poly-ether-ester-amide block copolymers, polyacrylates, polyacrylic acids, ionomers, polyethylene-vinyl acetate with a vinyl acetate content of more than 28 weight %, polyvinyl alcohol and its copolymers, polyvinyl ethers and their copolymers, poly-2-ethyl-oxazoline, polyvinyl pyrrolidone and its copolymers, and mixtures thereof, a suitable compatible hydrophilic plasticiser or blend of hydrophilic plasticisers.

said thermoplastic composition having a viscosity of from 50 poise to 4000 poise at a frequency of 1 rad/s at a temperature of 210° C. or less and a viscosity of less than 2000 poise at a frequency of 1000 rad/s at a temperature of 210° C. or less, wherein said compatible hydrophilic plasticiser are selected from the group consisting of acids, esters, amides, alcohols, polyalcohols, and mixtures thereof.

2. A shape-formed, three dimensional, moisture vapour permeable, liquid impermeable article according to claim 1, wherein said article comprises said structure, and wherein said structure is made of said thermoplastic composition, said structure having a water vapour transmission rate (WVTR) of at least 300 g/m$^2$·24 h with a thickness of said structure of at least 0.5 μm.

3. A shape-formed, three dimensional, moisture vapour permeable, liquid impermeable article according to claim 2, wherein said article is made of said structure.

4. A shape-formed, three dimensional, moisture vapour permeable, liquid impermeable article according to claim 1, wherein said article is a hand covering article.

5. A shape-formed, three dimensional, moisture vapour permeable, liquid impermeable article according to claim 4, wherein said article is a glove.

6. A process for making a shape-formed, three dimensional, moisture vapour permeable, liquid impermeable article according to claim 1, comprising the steps of:

providing said thermoplastic composition, forming said thermoplastic composition into said structure by means of a moulding, or casting, or coating method, forming said structure into said article.

7. A process according to claim 6, wherein said thermoplastic composition is provided in a solvent-based format, or in a hot-melt format, or in an emulsion-based format.

8. A process according to claim 6, wherein said process comprises the further step of:
   concurrently mating a second material with said thermoplastic composition when forming said thermoplastic composition into said structure, wherein said structure is a composite structure.

9. A process according to claim 8, wherein said second material comprises separate individual pieces.

10. A process according to claim 9, wherein said second material comprises flocking fibres in order to provide said composite structure with a flocking surface.

\* \* \* \* \*

UNITED STATES PATENT AND TRADEMARK OFFICE
CERTIFICATE OF CORRECTION

PATENT NO.    : 6,495,612 B1                                             Page 1 of 1
DATED         : December 17, 2002
INVENTOR(S)   : Italo Corzani et al It is certified that error appears in the above-identified patent and that said Letters Patent is hereby corrected as shown below:

<u>Title page,</u>
Item [86], after "PCT Pub. Date," "Nov. 16, 1999" has been replaced with -- Dec. 16, 1999 --.

<u>Column 12,</u>
Line 42, "plasticiser" has been replaced with -- plasticisers --.

Signed and Sealed this

Twenty-ninth Day of April, 2003

JAMES E. ROGAN
*Director of the United States Patent and Trademark Office*